United States Patent [19]

Pettit et al.

[11] Patent Number: 4,940,726
[45] Date of Patent: Jul. 10, 1990

[54] CELL GROWTH INHIBITORY MACROCYCLIC LACTONES DENOMINATED COMBRETASTATIN D-1 AND COMBRETASTATIN D-2

[75] Inventors: George R. Pettit, Paradise Valley; Sheo B. Singh, Tempe, both of Ariz.

[73] Assignee: Arizona Board of Regents, Tempe, Ariz.

[21] Appl. No.: 344,005

[22] Filed: Apr. 26, 1989

[51] Int. Cl.$^5$ .................. A61K 31/365; C07B 321/00
[52] U.S. Cl. ............................ 514/450; 514/908; 549/266; 549/267; 549/270
[58] Field of Search .............. 514/450, 908, 475; 549/266, 267, 270

[56] References Cited

U.S. PATENT DOCUMENTS 4,708,962 11/1987 Higa et al. .................. 514/475

OTHER PUBLICATIONS

G. Pettit, et al., *J. Am. Chem. Soc.*, "Isolation and Structure of Combretastatin D-1", 110(25), pp. 3539-3540 (1988).

*Primary Examiner*—Robert T. Bond
*Assistant Examiner*—Mark W. Russell
*Attorney, Agent, or Firm*—Richard R. Mybeck

[57] ABSTRACT

The isolation and elucidation of novel caffrane macrocyclic lactones denominated "Combretastatin D-1" and "Combretastatin D-2", each of which was found to possess unexpected cell growth inhibitory properties. The lactones have the structural formula:

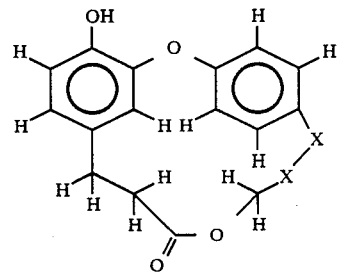

wherein:

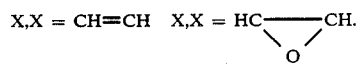

9 Claims, No Drawings

CELL GROWTH INHIBITORY MACROCYCLIC LACTONES DENOMINATED COMBRETASTATIN D-1 AND COMBRETASTATIN D-2

Part of the work embraced herein was funded by a grant CA-30311-01-03 from the National Cancer Institute and by the Arizona Disease Control Research Commission.

INTRODUCTION

The present invention relates to the isolation and elucidation of novel caffrane macrocyclic lactones denominated "Combretastatin D-1" and "Combretastatin D-2", each of which was found to possess unexpected cell growth inhibitory properties.

BACKGROUND OF THE INVENTION

Tropical and subtropical shrubs and trees of the Combretaceae family represent a practically unexplored reservoir of new substances with potentially useful biological properties. Illustrative is the genus Combretum with 25 species (10% of the total) known in the primitive medical practices of Africa and India for uses as diverse as treating leprosy (See: Watt, J. M. et al, "The Medicinal and Poisonous Plants of Southern and Eastern Africa", E. & S. Livingstone, Ltd., London, 1962, p. 194) (*Combretum sp.* root) and cancer (*Combretum latifolium*). But only a few species principally *Combretum micranthum* (used in northern Zimbabwe for mental illness) (See: Ogan, A. U., *Planta Medica*, 1972, 21, 210; and Malcolm, S. A. et al, Llovdia, 1969, 32, 512; *C. ZeVheri* (for scorpion invenomation); and Mwauluka, K. et al, *Biochem. Physiol. Pflanzen*, 1975, 168, 15) have received any scientific study.

The present investigation was undertaken to determine the murine P388 lymphocytic leukemia (PS system) inhibitory constituents of *Combretum caffrum* (Eckl. and Zeyh) Kuntze (also as *C. salicifolium* E. Mey), a potentially useful lead which came out of the U.S. National Cancer Institute's world-wide exploratory survey of plants. In South Africa this tree is known by the Zulu as "Mdubu" (used as a charm) and is known elsewhere as the "bushveld willow", the "bushwillow" and the "rooiblaar". The timber is principally used on African farms as scrap wood and fuel. Interestingly, honey obtained from the nectar of this tree is strongly bitter but no problems have been recorded from its human consumption.

BRIEF SUMMARY OF THE INVENTION

New cell growth inhibitory substances have been isolated from the South African tree Combretum caffrum (Combretaceae) and structures were elucidated. The substances are unexpected and unusual macrocyclic lactones, herein denominated Combretastatin D-1 and Combretastatin D-2, and have a PS cell line activity corresponding to $ED_{50}$ 3.3 and 5.2 μg/ml, respectfully.

The structure of each of the substances is as follows:

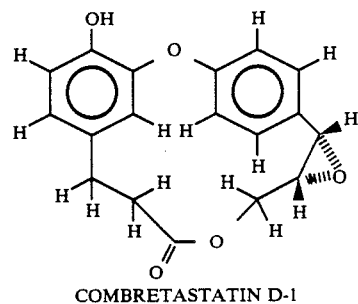

COMBRETASTATIN D-1

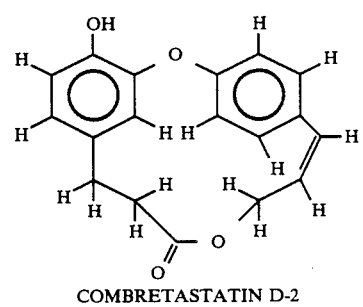

COMBRETASTATIN D-2

The substances can both be extracted from the stem wood of *Combretum caffrum* with 1:1 methylene chloride and thereafter converted to methylene chloride fraction which is partitioned between hexane and methanol-water followed by adjustment to 3:2 methanol-water and extraction with methylene chloride. The methylene chloride fraction is then separated by steric exclusion chromatography on SEPHADEX LH-20 to obtain the respective fractions. The isolation of the specific substances described herein from those respective fractions is detailed in the several examples reported below.

Accordingly, a principle object of the present invention is to isolate and elucidate the structure of new cell growth inhibitory substances from *Combretum caffrum* and to provide the methodology for the efficient and reliable replication thereof by synthetic procedures.

Another object of the present invention is to provide new and useful pharmaceutical preparations containing one of the new cell growth inhibiting substances as the essential pharmaceutically active ingredient thereof.

These and still further objects as shall hereinafter appear are fulfilled by the present invention in a remarkably unexpected fashion as will be readily discerned from a careful consideration of the following detailed description of preferred embodiments thereof, especially when read in conjunction with the several examples appended thereto.

DESCRIPTION OF PREFERRED EMBODIMENTS

The present invention relates to the isolation and structural elucidation of unexpected and unusual caffrane macrocyclic lactones herein designated as "Combretastatin D-1" "Combretastatin D-2". Both substances demonstrate PS cell line activity corresponding to $ED_{50}$ of 3.3 μg/mL and 5.2 μg/mL, respectfully. The combretastatins hereof have the following structure formula:

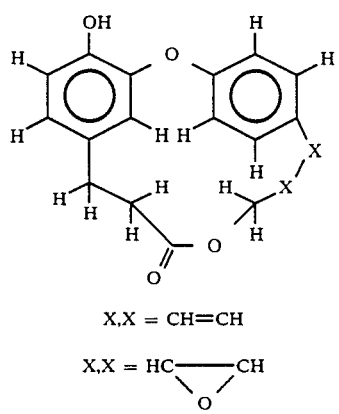

X,X = CH=CH

X,X = HC—CH
       \ /
        O

The methylene chloride-methanol extract obtained from 77 kg of Combretum caffrum stem wood was initially separated as described in *J. Nat. Products*, 1987 50 119; and *Can J. Chem*, 1987 65 2390. The fraction described therein which led to combretastatin A-2 was further separated guided by PS bioassay using a sequence of gel permeation, partition (SEPHADEX LH-20, hexane-toluene-methanol, 3:1:1) and silica gel flash chromatography employing hexane-chloroformacetone (3:2:0.25) as eluent to provide combretastatin D-1 in $2.3 \times 10^{-4}\%$ yield: 180 mg as needles from acetone-hexane; mp 180°–181° C., Rf 0.44 (SiO$_2$ plate; 1:1 hexane-ethyl acetate); $[\alpha]_D$-100° (c=0.015, CHCl$_3$), HREIMS (m/z) 312.0998 (M+, 100%, for C$_{18}$H$_{16}$O$_5$, calcd. 312.0998), 267.1015 (M+, -CO$_2$H, 22%), 253.0862 (M+-CH$_3$CO$_2$, 42%), 227.0712 (M+- C$_4$H$_5$O$_2$, 66%), 131.0496 (15%), 122.0368 (6%), and 119.0497 (10%). UV (CHCl$_3$) $\lambda_{max}$ 224 (E15215), 278 (3068) nm; IR (NaCl)$\lambda_{max}$ 3439, 3431, 3422, 3415, 1735, 1518, 1507, 1438, 1362, 1288, 1216, 1159, and 1142 cm$^{-1}$. The $^{13}$C-NMR and $^1$H-NMR assignments are shown in Table I below.

TABLE I $^{13}$C-NMR (100 MHz, δ, CDCl$_3$): 26.97 (C-15), 31.24 (C-16), 52.99 (C-3), 55.84 (C-4), 62.56 (C-2), 112.24 (C-20), 115.38 (C-12), 122.03 (C-13), 123.14 (C-19), 123.95 (C-7), 126.34 (C-18), 128.83 (C-6), 131.90 (C-5), 132.44 (C-14), 142.62 (C-11), 149.09 (C-10), 156.01 (C-8), and 172.53 (C-17) ppm. and $^1$H-NMR (400 MHz,δ, CDCl$_3$): 2.134 (1H, ddd, J=17.5, 12.5, 1.5 HZ, H-16α), 2.398 (1H, ddd, J=17.5, 6.0, 1.50 Hz, H-16β), 2.583 (1H, dd, J=16.8, 6.0 Hz, H-15α), 3.112 (1H, dd, J=16.8, 12.5 Hz, H-15β), 3.483 (1H, ddd, J=9.2, 4.5, 4.5 Hz, H-3), 3.871 (1H, dd, J=12.0, 9.2 Hz, H-2α), 4.264 (1H, dd, J=12.0, 4.5 Hz, H-2β), 4.355 (1H, d, J=4.5 Hz, H-4), 4.940 (1H, d, J=1.8 Hz, H-20), 5.486 (1H, brs, OH), 6.617 (1H, ddd, J=8.2, 1.8, 1.5 Hz, H-13), 6.836 (1H, d, J=8.0 Hz, H-12), 7.081 (1H, dd, J=8.0, 2.0 Hz, H-19), 7.104 (1H, dd, J=8.0, 2.0 Hz, H-7), 7.362 (1H, dd, J=8.0, 2.0 Hz, H-18), 7.549 (1H, dd, J=8.0, 2.0 Hz, H-6).

Mass spectral analysis of the lactone designated combretastatin D-1 revealed a molecular formula of C$_{18}$H$_{16}$O$_5$ with eleven double bond equivalents. Because of the absence of any isolated or conjugated double bonds, with the exception of two aromatic rings, it became apparent that this molecule possessed two additional rings and a lactone (IR: 1735 cm$^{-1}$). One ring was located as an epoxide while the other formed the skeletal cyclic system. The $^1$H-NMR spectrum was assigned using $^1$H, $^1$H-COSY techniques. Four isolated coupling patterns were observed. Long range (5 bonds) coupling was observed between H-16 (both α and β) and H-13. All the protons were further assigned on the basis of NOE experiments (magnitude of observed NOE's were 1→6%). Proton-20 (δ 4.940) was correlated to δ 112.24 in the carbon spectrum ($^1$H, $^{13}$C-COSY). Such exceptional shielding of an aromatic proton was attributed to its entrance into the shielding cone of the other aromatic ring. Support for this assumption and the structure of combretastatin D-1 was obtained by an X-ray crystal structure determination and examining the Dreiding model of this lactone. Restricted rotation between the two aromatic rings was apparent in the model. NOE experiments suggested that in solution the most stable conformation of the macrocycle also exists as presented in the structure shown above, i.e. the carbonyl group of the lactone faces away from the ring.

In the determination of the absolute configuration of combretastatin D-1, the absolute configuration of the epoxide ring was assigned (3R, 4S) by comparing the sign of the Cotton effect curves in the CD spectrum reported in Table II of the epoxide with Cotton effect curves of (1R, 2R)-(+)-1-phenylpropylene oxide and (1S, 2S)-(−)-1-phenyl-propylene oxide. The CD spectral assignments are shown in Table II.

TABLE II

CD spectra: CH$_3$OH: ε (nm) 0 (308), +13.4 (285), 0 (275), +5.9 (267), −34.2 (247), 0 (240)., (1R, 2R)-(+)-1-phenyl-propylene oxide, ε(nm) 0 (278), +0.15 (271), +0.07 (267), +0.16 (263), +0.09 (259), +0.11 (257), 0 (235).; (1S, 2S)-(−)-1-phenylpropylene oxide, ε(nm) 0 (278), −0.15 (271), −0.07 (267), −0.16 (263), −0.09 (259), −0.11 (257), 0 (235).

In one practice of the present invention, 77 kilograms of dry stem wood of Combretum caffrum is subdivided by chipping and thereafter extracted with 320 liters of 1:1 methylene chloride-methanol at ambient temperature for eleven days. The methylene chloride phase is then separated by the addition of water (approximately 25% by volume). The plant extraction is repeated with another 320 liters of 1:1 methylene chloride-methanol at ambient temperature for eleven days and the methylene chloride phase is separated therefrom by the addition of water, just as before.

The two methylene chloride phases so created are then combined and concentrated into a crude extract weighing 1.42 kilograms and showing PS (P388) in vivo life extension of 27% at 100 mg/Kg and PS ED$_{50}$ 5.1 μg/mL.

A solution of the methylene chloride fraction is partitioned five times between hexane (18 liters) and methanol-water (9:1, 18 liters). After separating the hexane phase, the methanol-water is adjusted to a concentration of 3:2 and extracted five times with methylene chloride (18 liters). The methylene chloride fraction from the solvent particularly sequence showed PS (P388) in vivo life extension of 38–41% at 25–50 mg/Kg and major cell growth inhibition (ED$_{50}$ 0.21 μg/mL).

The methylene chloride fraction is next dissolved in methanol (7×500 mL) and further separated by steric exclusion chromotography on columns of SEPHADEX LH-20 (7×2.5 kg). The PS active (41% life extension at 12.5 mg/kg and ED$_{50}$ 0.18 μg/mL) fraction A is further separated in hexane-toluene-methanol (3:1:1) solution by partition chromotography on SEPHADEX LH-20 (2.5 kg) to give an active fraction (0.54g PS $ED_{50}$ 1.9 μg/mL) which is rechromotographed over a silica gel flash column packed and eluted with hexane-chloroform-acetone (12:8:1) to provide combretastatin D-1.

Additional amounts of fraction A are further separated on a column of SEPHADEX LH-20 to provide a second active fraction (1.97 g, PS $ED_{50}$ $1.8 \times 10^{-2}$ μg/mL) that is redissolved in 3:1:1 hexane-toluene-methanol and the solution is filtered. The filtrate is then chromatographed on a SEPHADEX LH-20 column with a 3:1:1 hexane-toluene-methanol solvent system. The resulting active fraction (1.35g, PS $ED_{50}$ $2.4 \times 10^{-2}$ μg/mL) is dissolved in hexane-ethyl acetate (1:1) and chromotographed on a column (60×2.5 cm) of silica gel. Gradient elution from 4:1 → 1:1 hexane-ethyl acetate afforded in a 3:1 the next PS active material (0.7g, $ED_{50}$ $1.0 \times 10^{-2}$ μg/mL). This material is rechromotographed in acetone over a long column (100×1.2 mg) of silica gel using the gradient hexane-ethyl acetate 9:1 → 4:1 to yield in a 4:1 fraction a pure specimen of combretastatin D-2 (5.8 mg, $7.5 \times 10^{-6}\%$ yield based on the dried plant, PS $ED_{50}$ 5.2 μg/mL) crystallized from acetone-hexane, mp 148°–151° C. The IR and NMR data for this substance is shown in Example 4, infra.

The natural combretastatin active ingredients to be employed as cell growth inhibitory or antineoplastic agents can be easily prepared into appropriate unit dosage forms using pharmaceutical materials and established procedures which are well known in the art and need not be elaborated upon here. Illustrations of the preparation of some typical unit dosage forms, and not as limitation thereof, are set forth below.

The administration of combretastatin D-1 and D-2, their synthetic counterparts, and their pharmacologically active physiologically compatible derivatives is useful to treat animals or humans inflicted with a neoplastic disease which is treatable by the inhibition of the cell growth associated therewith. Typical of such diseases are: acute myelocytic leukemia; acute lymphocytic leukemia; malignant melanoma; adenocarcinoma of lung; breast carcinoma; colon carcinoma; ovarian carcinoma; bladder carcinoma and the like.

The dosage administered will be dependent upon the identity of the neoplastic disease and the idiosyncratic cell growth associated therewith; the type of host involved including its age, general state of health and weight; the kind of concurrent treatment, if any; and the frequency of treatment and therapeutic ratio.

Illustratively, dosage levels of the administered active ingredients, expressed as milligrams of active ingredient per kilogram of host body weight, are: intravenous, 0.1 to about 20 mg/kg; intramuscular, 1 to about 50 mg/kg; orally, 5 to about 100 mg/kg; intranasal instillation, 5 to about 100 mg/kg; and aerosol, 5 to about 100 mg/kg.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01 to about 50% w/w of the composition; preferably about 1 to about 20% w/w of the composition; and for parenteral use in a concentration of from about 0 05% to about 50% w/v of the composition and preferably from about 5% to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as a talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcuim phosphate and the like. The powder mixture can be granulated by wetting with a binder such as corn syrup, gelatin solution, methycellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously the tablet can be provided with a protective coating consisting of a sealing coat or enteric coat of shellac, a coating of sugar and methylcellulose and a polish coating of carnauba wax.

Fluid unit dosage forms for oral administration such as syrups, elixers and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixer is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable dial or ampule and sealing.

Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and the sterilization steps cannot be accomplished by filtration. With parenteral suspensions, the active ingredient is preferably sterilized by exposure to ethylene oxide before it is suspended in the sterile vehicle. Advantageously, a surfactant or wetting agent will be included in the composition to facilitate uniform distribution of the active ingredient.

In addition to oral and parenteral administration, rectal and vaginal routes can be utilized. An active ingredient can be administered by means of a suppository. A vehicle which has a melting point at or about body temperature or one that is readily soluble can be utilized. For example, cocoa butter and various polyethylene glycols (Carbowaxes) can serve as the vehicle for highly effective suppositories.

For intranasal instillation, a fluid unit dosage form is prepared utilizing an active ingredient and a suitable pharmaceutical vehicle, preferably pyrogen free ("P.F.") water. A dry powder can be formulated when insufflation is the administration of choice.

For use as aerosols, the active ingredients can be packaged in a pressurized aerosol container together with a gaseous or liquefied propellant, for example, dichloro-difluoromethane, carbon dioxide, nitrogen, propane, and the like, with the usual adjuvants, such as cosolvents and wetting agents, as may be necessary or desirable.

The term "unit dosage form" as used in the specification and claims hereof refers to physically discrete units suitable as unitary dosages for human and animal subjects, each unit containing a predetermined quantity of active material calculated to produce the desired therapeutic effect in association with the required pharmaceutical diluent, carrier or vehicle The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients hereof to be employed as cell growth inhibitory agents can be easily prepared in such unit dosage form with the employment of pharmaceutical materials which themselves are available in the art and can be prepared by established procedures which need not be repeated here.

To further assist in the understanding of the present invention and not by way of limitation the following examples are presented to more clearly disclose the present invention.

EXAMPLE I

Plant Taxonomy

Stem wood of the South African tree *Combretum caffrum* (Eckl. and Zeyh) Kuntze was collected and identified as part of the National Cancer Institute-U.S. Department of Agriculture research program directed by Drs. John D. Douros, Matthew I. Suffness and James A. Duke. The stem wood (B817373) employed in this study was obtained in 1979.

EXAMPLE 2

Extraction and Solvent Partition Procedures

The dry stem wood (77 kg) of *Combretum caffrum* was subdivided by chipping and extracted with 1:1 methylene chloride-methanol (320 liters) at ambient temperature for eleven days. The methylene chloride phase was separated by addition of water (25% by volume) and the plant extraction was repeated with another 320 liters of methylene chloride-methanol 1:1 as just described. The combined methylene chloride phases were concentrated to a crude extract weighing 1.42 kg and showing PS (P388) in vivo life extension of 27% at 100 mg/kg and PS $ED_{50}$ 5.1 µg/mL. A solution of the methylene chloride fraction was partitioned 5×between hexane (18 liters) and methanol-water (9:1, 18 liters). After separating the hexane phase the methanol-water was adjusted to a concentration of 3:2 and extracted (5x) with methylene chloride (18 liters). The hexane extract (602.3 g) proved PS in vivo inactive and marginally active against the cell line with $ED_{50}$ 2.4 µg/mL. The PS in vivo activity (38–41% life extension at 25–50 mg/kg) and major cell growth inhibition ($ED_{50}$ 0.21µg/mL) was concentrated in the methylene chloride fraction (827.9 g) from the solvent partitioning sequence.

EXAMPLE 3

Isolation of Combretastatin D 1

The methylene chloride fraction from the solvent partitioning sequence was dissolved in methanol (7×500 mL) and further separated by steric exclusion chromatography on columns of SEPHADEX LH-20 (7×2.5 kg). The PS active (41% life extension at 12.5 mg/kg and $ED_{50}$ 0.18 µg/mL fraction A (28.6 g) was further separated in hexane-toluene-methanol (3:1:1) solution by partition chromatography on SEPHADEX LH-20 (2.5 kg) to give an active fraction (0.54 g, PS $ED_{50}$ 1.9 µg/mL) which is rechromatographed over a silica gel (0.04–0.063µ) flash column (3.0 cm×20.0 cm). The column was packed and eluted with hexane-chloroform-acetone (3:2:0.25) which yielded combretastatin D-1 in $2.3\times10^{-4}$% yield: 180 mg as needles from acetone-hexane; mp 180°–181° C.

EXAMPLE 4

Isolation of Combretastatin D-2

Fraction A (28.6 g) was further separated on a column of SEPHADEX LH-20 (2.5 kg) by partition chromatography employing hexane-toluene-methanol (3:1:1) to furnish an active fraction (1.97 g, PS $ED_{50}$ $1.8\times10^{-2}$ µg/ml) that was redissolved in 3:1:1 hexane-toluene-methanol (20 ml) and the solution was filtered. The filtrate was chromatographed on a SEPHADEX LH-20 (200 g) column with the same solvent system. The resulting active fraction (1.35 g, PS $ED_{50}$ $2.4\times10^{-2}$ µg/ml) was dissolved in hexane-ethyl acetate (1:1, 5ml) and chromatographed on a column (60×2.5 cm) of silica gel (60 g). Gradient elution from 4:1→1:1 hexane-ethyl acetate; afforded in a 3:1 fraction the next PS (0.7 g, $ED_{50}$ $1.0\times10^{-2}$ µg/ml) active material Rechromatography in acetone (2 ml) over a long column (100×1.2 mg) of silica gel (45 g) using the gradient hexane-ethyl acetate 9:1→4:1 yielded in a 4:1 fraction a pure specimen of combretastatin D-2 (5.8, $7.5 \times 10^{-6}$%, yield based on the dried plant, PS $ED_{50}$ 52 μg/ml), crystallized from acetone-hexane, mp 148–151° C., IR (NaCl)$\nu_{max}$ 3436, 3429, 1728, 1519, 1503, 1440, 1215, 1186, 1159, 1110 cm$^{-1}$, $^1$H-NMR (400 MHz) CDCl$_3$: 2.289 (2H, d$^t$, J=5.0, 1.7 Hz, H-16), 2.871 (2H, t, J=5.0 Hz, H-15), 4.640 (2H, d, J=6.8 Hz, H-2), 5.066 (1H, d, J=1.8 Hz, H-20), 5.467 (1H, s, OH), 6.064 (1H, dt, J=10.6, 6.8 Hz, H-3), 6.634 (1H, ddd, J=8.0, 1.8, 1.7 Hz, H-13), 6.846 (1H, d, J=8.0 Hz, H-12), 7.089 (2H, d, J=8.4 Hz, H-7, 19), 7.112 (1H, d, J=10.6 Hz, H-4), 7.329 (2H, d, J=8.4 Hz, H-6, 18); $^{13}$C-NMR (100 MHz) CDCl$_3$: 26.89 (c-15), 32.42 (c-16), 59.06 (c-2), 112.58 (c-20), 115.39 (c-12), 121.89 (c-13), 123.89 (c-7, 19), 125.68 (c-18), 129.09 (C-6), 131.14, 132.01 (c-5, 14), 135.45 (c-4), 137.74 (c-3), 142.48, 149.32 (c-10, 11), 155.6 (c-8), 173.30 (c-17), and HREIMS (m/z) 296.1052 (M$^+$, 100%, calcd. for C$_{18}$H$_{16}$O$_4$: 296.1049); 237.0916 (20%, calcd. for C$_{16}$H$_{13}$O$_2$: 237.0916 M$^+$−CH$_3$CO$_2$); 138.0321 (46%, calcd. for C$_7$H$_6$O$_3$: 138.0317); 135.0450 (50%, calcd. for C$_8$H$_7$O$_2$: 135.0446).

EXAMPLE 5

Combretastatin D-1 was subjected to the standard National Cancer Institut.e protocol for murine P388 lymphocytic leukemia (PS System) and provided a PS cell line activity of $ED_{50}$=3.3 μg/ml.

EXAMPLE 6

Combretastatin D-2 was subjected to the standard National Cancer Institute protocol for murine P388 lymphocytic leukemia (PS System) and provided a PS cell line activity of $ED_{50}$=5.2 μg/ml.

From the foregoing it is readily apparent that new and unique caffrane macrocyclic lactones have been herein described and illustrated, each of which was found to possess unexpected cell growth inhibitory properties and fulfills all of the aforestated objects in a remarkably unexpected fashion. It is of course understood that such modification, alterations and adaptations that may readily occur to the artisan confronted with this disclosure are intended within the spirit of the present invention which is limited only by the scope of the claims appended hereto.

Accordingly, what is claimed is:

1. A cell growth inhibitory macrocyclic lactone having the structural formula:

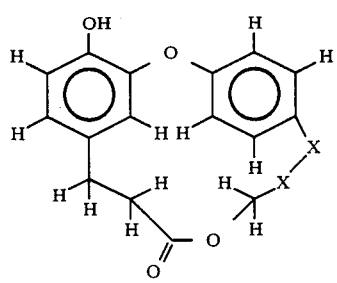

wherein:

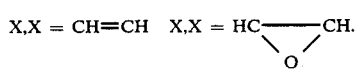

2. A macrocyclic lactone according to claim 1 denominated combretastatin D-1 and having the structural formula:

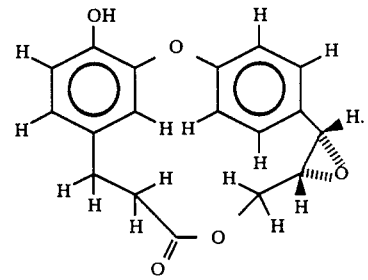

3. A macrocyclic lactone according to claim 1 denominated combretastatin D-2 and having the structural formula:

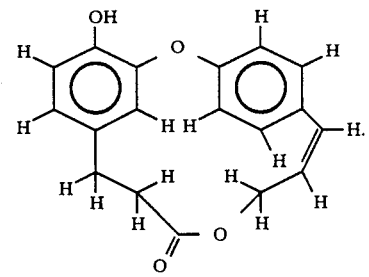

4. The method of treating a host afflicted with a neoplastic disease characterized by uncontrolled cell growth comprising administering to said host a pharmaceutical preparation containing a pharmacologically acceptable carrier and, as its essential active cell growth inhibitory substance a therapeutically active amount of a macrocyclic lactone having the structural formula:

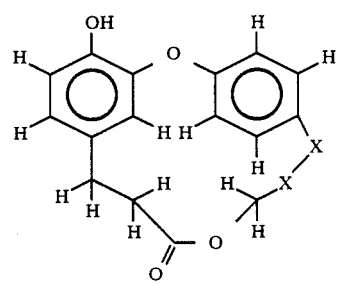

wherein:

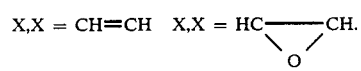

5. The method of claim 4 in which said macrocyclic lactone is denominated combretastatin D-1 and X,X is

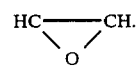

6. The method of claim 4 in which said macrocyclic lactone is denominated combretastatin D-2 and X, X is CH=CH.

7. A pharmaceutical preparation comprising a pharmacologically acceptable carrier and a pharmaceutically effective amount of a cell growth inhibitory macrocyclic lactone having the structural formula:

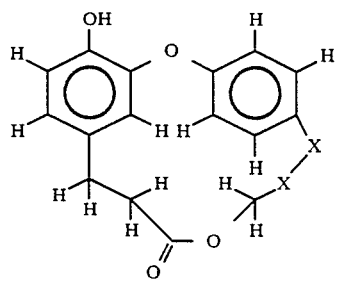

wherein:

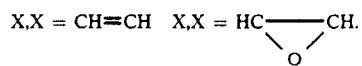

8. A pharmaceutical preparation according to claim 7 in which said macrocyclic lactone is combretastatin D-1 and X,X is

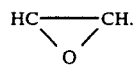

9. A pharmaceutical preparation according to claim 7 in which said macrocyclic lactone is combretastain D-2 and X,X is CH=CH.

* * * * *